（12） United States Patent
Feraud et al.

(10) Patent No.: US 8,815,850 B2
(45) Date of Patent: Aug. 26, 2014

(54) PROCESS FOR PREPARING DIAMINOPHENOTHIAZINIUM COMPOUNDS

(75) Inventors: Michel Feraud, Marseilles (FR); Babak Sayah, Marseilles (FR)

(73) Assignee: Provence Technologies, Marseilles (FR)

( * ) Notice: Subject to any disclaimer, the term of this patent is extended or adjusted under 35 U.S.C. 154(b) by 0 days.

(21) Appl. No.: 13/552,738

(22) Filed: Jul. 19, 2012

(65) Prior Publication Data

US 2013/0005713 A1 Jan. 3, 2013

Related U.S. Application Data

(62) Division of application No. 12/373,194, filed as application No. PCT/FR2007/001193 on Jul. 12, 2007.

(30) Foreign Application Priority Data

Jul. 12, 2006 (FR) ...................... 06 06330

(51) Int. Cl.
C07D 279/18 (2006.01)

(52) U.S. Cl.
USPC ........................................ 514/224.8; 544/36

(58) Field of Classification Search
CPC .................................................. C07D 279/18
USPC .......................................................... 544/36
See application file for complete search history.

(56) References Cited

U.S. PATENT DOCUMENTS

| 4,212,971 | A | 7/1980 | Randvere et al. |
| 7,790,881 | B2 | 9/2010 | Storey et al. |
| 7,956,183 | B2 | 6/2011 | Wischik et al. |
| 2011/0294795 | A1 | 12/2011 | Wischik et al. |

FOREIGN PATENT DOCUMENTS

| AU | 2007 274057 | 1/2008 |
| DE | 1886 C | 12/1877 |
| FR | 2 810 318 A1 | 12/2001 |
| GB | 2 373 787 A | 3/2011 |
| WO | WO 03/082296 A1 | 10/2003 |
| WO | WO 2005/054217 | 6/2005 |
| WO | WO 2006/032879 A2 | 3/2006 |
| WO | WO 2008/007074 A2 | 1/2008 |

OTHER PUBLICATIONS

International Search Report and Written Opinion for PCT/FR2007/001193 filed Jul. 12, 2007.
Database Beilstein Crossfire; Beilstein Institute of Organic Chemistry; Reaction ID: 5575384 1899, XP002461752; vol. 237, 1899, p. 387.
Database Beilstein Crossfire; Beilstein Institute of Organic Chemistry; Reaction ID: 5575388; XP002461753; vol. 231, 1899, p. 387.
Gensler, Walter J. et al: "Hydrolysis and autoxidation of N-benzoylleucomethylene blue"; Journal of Organic Chemistry, 31(7); 2324-30; CODEN: JOCEAH; ISSN: 0022-3263; 1966; XP002461751; p. 2327.
Silva et al., *Efficient Microwave-Assisted Synthesis of Tetrahydroindazoles and their Oxidation to Indazoles*, Synlett, 9 (2006) 1369-1373.
Office Action for Australian Application No. 2007274213 dated Jul. 16, 2012.
United States Pharmacopeia 2000, p. 1085, published Jan. 2000.
British Pharmacopeia 2000, pp. 1147-1148, published Jan. 2002.
British Pharmacopeia 2004, pp. 1294-1296, published 2004.
Leventis, N. et al., Tetrahedron 53 (29), (1997) 1083-1092.
Fiez, D. et al., *Fundamental Processes of Dye Chemistry*, Interscience (1994) 308-314.
Ju, H. et al., *The Electrochemical Behavior of Methylene Blue at a Microcylinder Carbon Fiber Electrode*, Electroanalysis 7, No. 12 (1995), 7 pages.
Marshall, P. N. et al., *The Purification of Methylene Blue and Azure B by Solvent Extraction and Crystallization*, Stain Technology, vol. 50, No. 6 (1976) pp. 375-381.
Nerenberg, C. et al., *Purification of Thionin, Azure A, Azure B and Methylene Blue*, vol. 38, No. 2 (1963), pp. 73-84.
Garrett, C. E., et al.; "*The Art of Meeting Palladium Specification in Active Pharmaceutical Ingredients Produced by Pd-Catalyzed Reactions;*" Advanced Synthesis & Catalysis; vol. 346; pp. 889-900; dated Apr. 2004.

(Continued)

Primary Examiner — Brian McDowell
(74) Attorney, Agent, or Firm — Alston & Bird LLP

(57) ABSTRACT

Process for preparing compounds of the diaminophenothiazinium type of formula (II) below. The products have a high degree of purity and are useful for the preparation of medicaments.

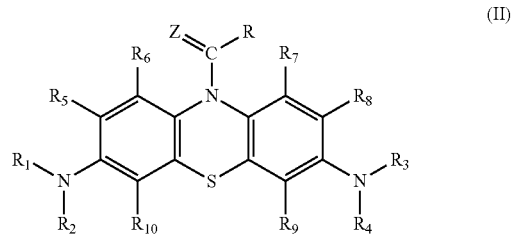

In which the $R_1$, $R_2$, $R_3$, $R_4$, $R_5$, $R_6$, $R_7$, $R_8$, $R_9$ and $R_{10}$ groups having the same definition as in formula (I), and R representing a group chosen from:
  a phenyl or benzyl group, optionally substituted with one or more functions chosen from: a $C_1$-$C_4$ alkyl, a halogen atom, a $C_1$-$C_4$ haloalkyl and a nitro group,
  a linear, branched or cyclic $C_1$-$C_8$ alkyl group,
  a $C_1$-$C_8$ alkylamino group,
  a $C_1$-$C_8$ alkoxy group,
  a phenyloxy or benzyloxy group optionally substituted on the aromatic nucleus with one or more functions chosen from: a $C_1$-$C_4$ alkyl, a halogen atom, a $C_1$-$C_4$ haloalkyl and a nitro group,
Z representing an atom chosen from O and S.

14 Claims, 1 Drawing Sheet

(56) References Cited

OTHER PUBLICATIONS

Königsberger, K., et al.; "*A Practical Synthesis of 6-[2-(2, 5-Dimethoxyphenyl)ethyl]-4-ethylquinazoline and the Art of Removing Palladium from the Products of Pd-Catalyzed Reactions*;" Organic Process Research & Development, vol. 7, No. 5; pp. 733-742; dated 2003.

Larsen, R. D., et al.; "*Efficient Synthesis of Losartan, a Nonpeptide Angiotensin II Receptor Antagonist*;" Journal of Organic Chemistry, vol. 59, No. 21; pp. 6391-6394; dated Apr. 1994.

Welch, C. J., et al.; "*Microplate evaluation of process adsorbents*;" Journal of Separation Science, vol. 25; pp. 847-850; dated Apr. 2002.

Synthetic scheme for methylene blue
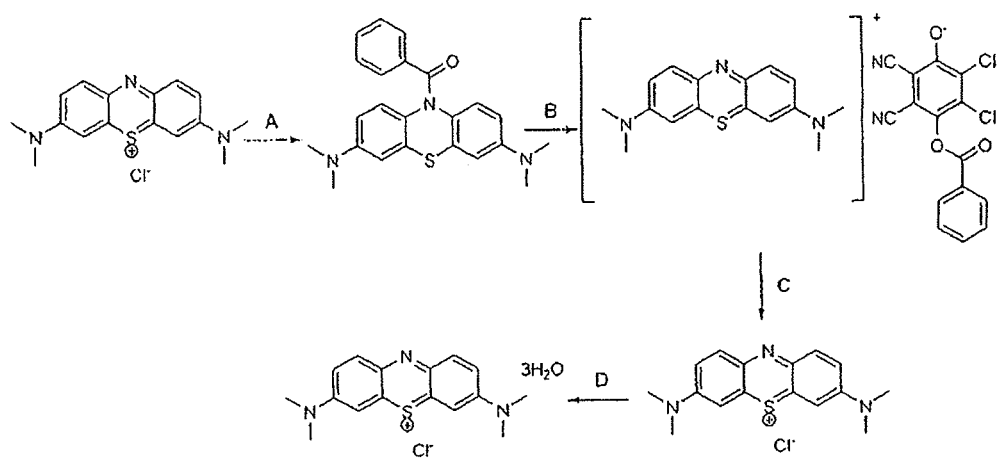
A. $H_2O/Na_2SO_4$, NaOH, Benzoyl chloride
B. $DDQ/CH_3CN$
C. Ion exchange then $NaOH/H_2O$ pH 4
D. Hydration ($H_2O$)

PROCESS FOR PREPARING DIAMINOPHENOTHIAZINIUM COMPOUNDS

CROSS REFERENCE TO RELATED APPLICATIONS

This application is a divisional application of application Ser. No. 12/373,194, filed Jun. 3, 2009, which is a national phase of PCT/FR2007/001193, filed Jul. 12, 2007, which claims priority from French Application No. 06 06330 filed Jul. 12, 2006.

FIELD AND BACKGROUND OF THE INVENTION

The subject of the present invention is a novel process for preparing compounds of the diaminophenothiazinium type, in particular a process for purifying these compounds. It relates in particular to methylene blue, and the subject thereof is also the products resulting from this process, the degree of purity of which is higher than those known in the prior art. A subject of the present invention is also the use of these compounds for the preparation of medicaments.

Methylthioninium chloride, also known as methylene blue or 3,7-bis(dimethylamino)phenothiazin-5-ylium chloride, is an organic compound corresponding to the formula below:

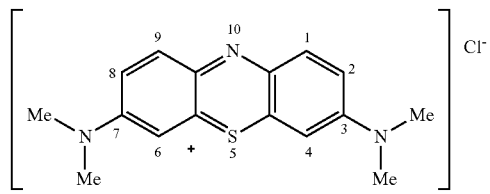

This compound has for a long time been used as a redox indicator and dye, as an optical developer in biophysical systems, in nanoporous materials as a separating material, and in photoelectrochromic imaging. It is also known for its uses as an antiseptic, antiinfective, as an antidote and as a diagnostic agent. It finds uses in particular in gynecology, neonatology, cancerology, oncology, urology, ophthalmology and gastroenterology. New uses in the therapeutic field are in the process of being developed, such as the reduction of pathogenic contaminants in the blood (GB2373787), or the prevention or inhibition of an exaggerated hemodynamic reaction (WO03/082296).

Many methods of synthesis have been described for this compound, since the oldest in 1877 (German patent No. 1886). All these methods have in common the fact of using metal compounds in at least one synthetic step:

Patent DE-1886 describes a process in which oxidative coupling of N,N-dimethyl-1,4-diaminobenzene is carried out with $H_2S$ and $FeCl_3$.

Fiez David et al., "Fundamental Processes of Dye Chemistry", 1949, Interscience, 308-314 describes a process in which the thiazine ring is formed by treatment with manganese dioxide or with copper sulfate. This process also comprises a treatment with zinc chloride, with sodium dichromate and with aluminum thiosulfate.

Document WO 2005/054217 describes methylene blue derivatives and a process for the preparation thereof. The method for preparing these compounds uses phenothiazine as starting product. Now, all the known methods for preparing phenothiazine call for metal reactants of which the metal atoms chelate the phenothiazine at the end of the synthesis. The products obtained by means of this process are therefore naturally contaminated with metal residues, in addition to the usual organic contaminants such as azure B.

Document WO 2006/032879 describes a process for preparing methylene blue which comprises a reduction step with iron, an oxidation step with sodium dichromate and an oxidation step with copper sulfate.

These processes require tedious and expensive purifications to be carried out in order to reduce the impurities, in particular the metal impurities of methylene blue. Despite the subsequent purification steps, these various processes inevitably produce a methylene blue comprising many metal impurities and also organic impurities, in particular azure B, azure C and azure A.

Document WO 2006/032879 asserts that it is possible to achieve a level of metal impurities representing 10% of the maximum threshold fixed by the European Pharmacopeia, but, according to the examples, it is noted that this level is not obtained simultaneously for all metals, and the results of the purification steps are not always reproducible. A detailed analysis of the metal contents of various commercially available methylene blues is illustrated in this document.

The European Pharmacopeia was recently amended (April 2006) in terms of an increase in the tolerance thresholds for metal impurities since no producer of methylene blue was able to produce, and even less to produce in an industrial amount, a methylene blue of a quality meeting its previous requirements.

SUMMARY OF THE INVENTION

A first subject of the invention was therefore the development of a process for preparing methylene blue which provides access to a highly pure methylene blue, in particular which comprises a very low level of metal and organic impurities, which can be extrapolated to an industrial scale under satisfactory economic conditions and which is not subject to variations in quality. According to one variant, the process of the invention is a process for purifying methylene blue.

The process which has been developed applies not only to methylene blue, but also to other derivatives of diaminophenothiazinium type.

The process of the invention is a process for preparing compounds corresponding to formula (I) below:

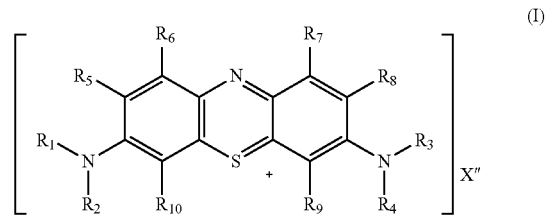

in which each of $R_1$, $R_2$, $R_3$, $R_4$, $R_5$, $R_6$, $R_7$, $R_8$, $R_9$ and $R_{10}$ may be chosen, independently of the others, from the group constituted of:

a hydrogen atom, saturated or unsaturated, linear, branched or cyclic $C_1$-$C_6$ alkyl groups, optionally substituted with one or more functions chosen from a halogen atom, and a $C_1$-$C_6$ alkoxy, $C_1$-$C_6$ alkyloxycarbonyl or —$CONH_2$ function, aryl groups optionally substituted with one or more functions chosen from: a $C_1$-$C_4$ alkyl, a halogen atom, and a $C_1$-$C_6$ alkoxy, $C_1$-$C_6$ alkyloxycarbonyl or —$CONH_2$ function, it being understood that two Ri groups (i=1, 2 ... 10) placed successively in FIG. (I) may be joined to form a ring. For example, $R_1$ with $R_5$, or $R_5$ with $R_6$, $R_7$ with $R_8$, $R_8$ with $R_3$, $R_3$ with $R_4$, $R_4$ with $R_9$, $R_{10}$ with $R_2$, or $R_2$ with $R_1$ may consist of a single alkyl chain which is optionally substituted, so as to form a fourth ring, in addition, each of $R_5$, $R_6$, $R_7$, $R_8$, $R_9$ and $R_{10}$ may be chosen, independently of the others, from the halogen atoms: F, Cl, Br and I, $X^-$ represents an organic or inorganic anion.

The anions that can be used include, for example, the anions of inorganic acids such as, for example, hydrochloric acid, hydrobromic acid, sulfuric acid, phosphoric acid or nitric acid; the anions of organic acids such as, for example, acetic acid, trifluoroacetic acid, oxalic acid, tartaric acid, succinic acid, maleic acid, fumaric acid, gluconic acid, citric acid, malic acid, ascorbic acid or benzoic acid; they also include $OH^-$.

This process is characterized in that it comprises at least one step during which a compound of formula (II):

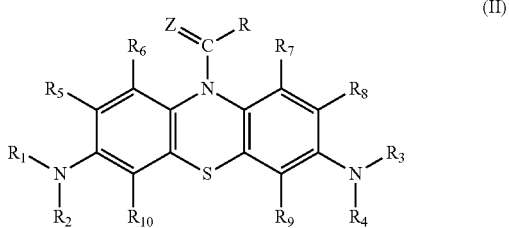

(II)

is subjected to a purification step under conditions which make it possible to separate metal compounds from the compounds of formula (II), the $R_1$, $R_2$, $R_3$, $R_4$, $R_5$, $R_6$, $R_7$, $R_8$, $R_9$ and $R_{10}$ groups having the same definition as in formula (I), and R representing a group chosen from:
- a phenyl or benzyl group, optionally substituted with one or more functions chosen from: a $C_1$-$C_4$ alkyl, a halogen atom, a $C_1$-$C_4$ haloalkyl and a nitro group,
- a linear, branched or cyclic $C_1$-$C_8$ alkyl group,
- a $C_1$-$C_8$ alkylamino group,
- a $C_1$-$C_8$ alkoxy group,
- a phenyloxy or benzyloxy group optionally substituted on the aromatic nucleus with one or more functions chosen from: a $C_1$-$C_4$ alkyl, a halogen atom, a $C_1$-$C_4$ haloalkyl and a nitro group, Z representing an atom chosen from O and S.

The purification of the compounds of formula (II) is carried out under conditions which make it possible to separate the metal compounds from the compounds of formula (II): filtration through a support capable of retaining the metal compounds, crystallization from an appropriate solvent, or any other method known to those skilled in the art.

When the purification is carried out by filtration through a support capable of retaining the metal compounds, such a support may be chosen from: a silica gel, an alumina gel (neutral, basic or acidic), an optionally modified diatomite, celite, a microporous membrane, resins grafted with metal-capturing groups and fibers grafted with metal-capturing groups, such as thiol, carboxylic acid or tertiary amine functions, or any other support having the property of retaining metals. Among the grafted fibers, mention may in particular be made of the products sold by the company Johnson Matthey under the trademark Smopex®. Among the diatomites, mention may be made of the products sold by the company CECA under the trademark Clarcel®.

The compound of formula (II) may be obtained starting from the compound of formula (I), by reduction of the compound of formula (I) and then by reaction of the amine function of the phenothiazinium ring with a suitable protective group R—CZ—Y in which R and Z have the same definition as above and Y represents a leaving group chosen from: a halogen atom such as F, Cl, I or Br, a $C_1$-$C_6$ alkoxy group, a —OCOR (anhydride) group, and a hydroxyl group, optionally in the presence of an activator of the dicyclohexylcarbodiimide (DCC) type. Advantageously, R is chosen from a phenyl group and a toluoyl group.

When the compound of formula (II) is obtained starting from the compound of formula (I), the overall process is a purification of the compound of formula (I). However, the compound of formula (II) may be obtained by means of other processes which do not use the product (I) as starting product.

Some compounds of formula (II), such as benzoyl leuco methylene blue, are commercially available.

The compound represented by formula (I) may be represented by several equivalent resonant structures. By way of nonlimiting illustration, represented below are other structures which are equivalent to that of formula (I):

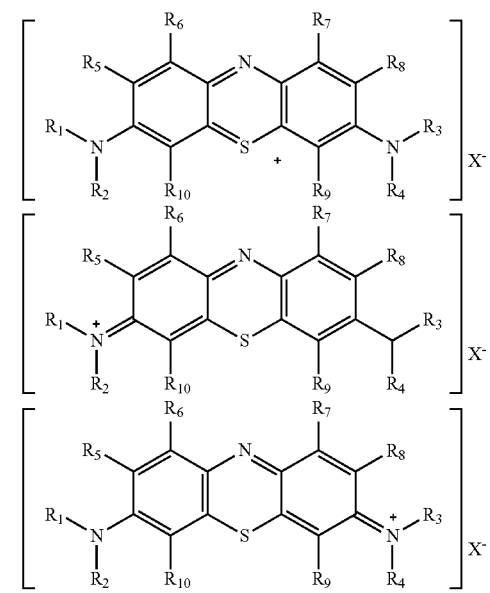

In formula (I) and in formula (II), $R_1$, $R_2$, $R_3$, $R_4$, $R_5$, $R_6$, $R_7$, $R_8$, $R_9$ and $R_{10}$, which may be identical or different, are preferably chosen from a hydrogen atom and a $C_1$-$C_4$ alkyl. Advantageously, $R_5$, $R_8$, $R_9$ and $R_{10}$ represent H.

More advantageously, one or more of the following requirements are met:
- X represents Cl or OH,
- $R_1$, $R_2$, $R_3$ and $R_4$, which may be identical or different, are chosen from a hydrogen atom and methyl,
- $R_6$ represents a hydrogen atom,
- $R_7$ represents a hydrogen atom,
- Z represents O.

Advantageously, the compound of formula (I) is tetramethylthionine chloride or methylene blue.

According to another variant, the compound of formula (I) is dimethylthionine chloride or Azure A, or trimethylthionine chloride or Azure B, or monomethylthionine chloride or Azure C.

BRIEF DESCRIPTION OF THE FIGURES

FIG. 1 is a synthetic scheme for the production of methylene blue.

DETAILED DESCRIPTION

According to the invention, the process for preparing the compound of formula (I) comprises at least one step for purification of a compound of formula (II); in particular, this purification comprises at least one step for filtration of a compound of formula (II) through a support capable of retaining metal compounds, such as a silica gel, an alumina gel (neutral, basic or acidic), an optionally modified diatomite, a resin functionalized with metal-capturing agents, fibers functionalized with metal-capturing agents, celite, a microporous membrane or any other support capable of retaining metal compounds.

In greater detail, according to this variant, the compound of formula (II) is solubilized in an appropriate solvent, and a filter is prepared with the filtration support which is introduced into an appropriate receptacle, such as a glass column, a sintered glass filter or an industrial spin-dryer. The receptacle packed with the chosen filtration support is moistened, preferably with the same solvent as that in which the compound of formula (II) is dissolved.

The solution containing the compound of formula (II) is deposited on the filter, the solution which passes through the filter is recovered, and the filter is rinsed several times with a solvent which may be identical to or different than that having served to solubilize the compound of formula (II). The eluted fractions are recovered and optionally concentrated.

Among the solvents that can be used to solubilize the compounds of formula (II), mention may preferably be made of: chlorinated solvents, for instance dichloromethane or chloroform, alcohols such as isopropanol, ethanol or methanol, or acetonitrile, ethyl acetate or tetrahydrofuran, or a mixture of these solvents.

The solution of the compound of formula (I) is advantageously of a concentration ranging from 1 g/l to $10^3$ g/l. Lower concentrations result in the use of solvent volumes that are too large, with consequences regarding the safety and the size of the material. Higher concentrations are difficult to envision owing to the solubility of the products.

It is envisioned to use approximately 0.1 to 10 kg of filtration support per kg of product to be filtered. It is advantageously envisioned to rinse the filter with 0.1 to 50 l of solvent per kg of product of formula (II) until complete elution of the product of formula (II). The process of the invention has the advantage of freeing the product of formula (II) of its metal impurities.

When it is chosen to purify the compound of formula (II) by crystallization, a solvent is advantageously chosen from: an alcohol such as ethanol and a chlorinated solvent such as methylene chloride.

Advantageously, the compound of formula (II) is produced starting from the compound of formula (I) which is reacted with a protective group R—CZ—Y in which Y is advantageously chosen from: F, Cl, Br, I, a $C_1$-$C_6$ alkoxy group, an —OCOR (anhydride) group, and a hydroxyl group, optionally in the presence of an activator of the dicyclohexylcarbodiimide (DCC) type.

The reaction is carried out conventionally in a basic or neutral medium in water or in a mixture of water and another solvent such as, for example, acetonitrile, tetrahydrofuran, dichloromethane or any other appropriate organic solvent.

The reaction is exothermic, and cooling means which make it possible to maintain the temperature of the mixture at about ambient temperature are preferably used.

The starting product (I) is either commercially available or is prepared by known methods, such as those described in WO 2006/032879.

In general, the products of formula (I) are prepared by means of synthetic processes which call for the use of metal derivatives which are found as impurities in the products (I). This is the case of methylene blue, but also of azure A, of azure B and of azure C.

The compounds of formula (I) cannot be freed of their metal and organic impurities directly, simply and efficiently. The prior art methods call for successive recrystallizations which do not have satisfactory yields and which produce products for which the level of residual impurities is difficult to control.

In addition, the products of formula (I) have the property of chelating metals, whereas the products (II) are nonchelating. The purification thereof is therefore much more efficient that the direct purification of the compounds of formula (I).

In the various steps of the process of the invention, care is taken to use non-metal materials and reactants and solvents devoid of metal residues so as not to introduce any external contamination.

After the product of formula (II) has been purified, in particular subjected to a filtration, according to the process of the invention, a step for deprotection of the amine of the phenothiazine ring of the compound of formula (II) is advantageously carried out. This deprotection is carried out by any means known to those skilled in the art, while avoiding the introduction of metal contaminants and under conditions which prevent degradation of the compound of formula (I). Among the means that can be used for the deprotection of the R—CZ-group, mention may be made of: quinones, for instance 2,3-dichloro-5,6-dicyano-1,4-benzoquinone (DDQ), $HNO_3$, $HClO_4$, $I_2$, HCl, $H_2SO_4$, $H_2O_2$, and a treatment with ultraviolet radiation. A quinone is preferably used for this step, and very preferably 2,3-dichloro-5,6-dicyano-1,4-benzoquinone. Advantageously, this deprotection reaction is carried out in a solvent chosen from: ethyl acetate, acetonitrile, tetrahydrofuran and acetone. The solvent preferred for this step is acetonitrile.

Advantageous deprotection conditions make provision for the use of from 0.80 to 1.1 molar equivalents of DDQ relative to the compound (II), even more advantageously from 0.85 to 1.05 molar equivalents of DDQ relative to the compound (II), advantageously from 0.90 to 1 molar equivalent. Preferably, this deprotection is carried out at a temperature of between −40° C. and −5° C. Although not completely excluded, a lower temperature would have the drawback of lengthening the reaction times, and a higher temperature could lead to the formation of by-products.

Depending on the means of deprotection used, it may be necessary to carry out an ion exchange in order to obtain the compound of formula (I) comprising the desired $X^-$ anion. Preferably, this ion exchange is carried out by treatment with HCl, advantageously in ethyl acetate. Other solvents could be used, but some are capable of leading to the formation of by-products.

The conditions for deprotection of the compounds of formula (II) disclosed above are particularly advantageous in that they make it possible to achieve a compound of formula (I) without introducing metal impurities during this step or forming organic impurities. According to one variant of the invention, it may be envisioned to purify the compound of formula (II) by means other than filtration on a support capable of retaining metals, for instance by crystallization from an appropriate solvent. According to this variant, the compound of formula (II) is subsequently deprotected using any deprotection means not involving the use of metal compounds, in particular using a quinone, in particular DDQ, preferably under the conditions disclosed above.

Another subject of the invention is therefore a process for preparing compounds corresponding to formula (I) described above, characterized in that it comprises at least one step for deprotection of the R—CZ-group of the amine of the phenothiazine ring of the compound of formula (II) using deprotection means not involving the use of metal compounds.

The expression "deprotection means not involving the use of metal compounds" is intended to mean the use of non-metal reactants, and of solvents not comprising metal residues (preferably <0.01 ppm), in reactors not comprising any metal parts, for instance enameled reactors.

Among the means that can be used for the deprotection of the R—CZ-group, mention may be made of: quinones, for instance 2,3-dichloro-5,6-dicyano-1,4-benzoquinone (DDQ), $HNO_3$, $HClO_4$, $I_2$, HCl, $H_2SO_4$, $H_2O_2$, and a treatment with ultraviolet radiation. A quinone is preferably used for this step, and very preferably 2,3-dichloro-5,6-dicyano-1,4-benzoquinone. Advantageously, the conditions for using DDQ which were described above are employed.

The method for deprotection of the compound (II) so as to give the compound (I) makes it possible to achieve a compound (I) which does not comprise any additional metal impurities compared with the product (II). In addition, these deprotection conditions prevent the formation of organic degradation products. In fact, the compounds of formula (I) have a limited stability and the use of certain treatment conditions results in degradations, for example of methylene blue to Azure A, B and C which are then difficult to separate.

The process of the invention makes it possible to have access to a compound of formula (I) which is devoid of metal contaminants and which has a high chemical purity, in a manner which is reliable, reproducible and applicable on an industrial scale. These qualities are essential for being able to provide a product of formula (I) of pharmaceutical quality.

In particular, the preparation or purification process of the invention is the only one which makes it possible to obtain, in industrial amounts and reproducibly, a methylene blue or tetramethylthionine chloride which comprises 0.02 μg/g or less of cadmium per g of methylene blue. Such a product constitutes another subject of the invention.

Another subject of the invention is a methylene blue or tetramethylthionine chloride which has a degree of purity of greater than 97%, preferably greater than 98%, even better greater than 99%, measured by HPLC (high performance liquid chromatography) under the conditions of the European Pharmacopeia 5.4 (edition of April 2006) and which comprises less than 4.5 μg/g of aluminum, advantageously less than 3 μg/g of aluminum, even more advantageously less than 2.5 μg/g of aluminum per g of methylene blue.

The process of the invention is also the only one to give access to a methylene blue or tetramethylthionine chloride which has a degree of purity of greater than 97%, preferably greater than 98%, even better greater than 99%, measured by HPLC under the conditions of the European Pharmacopeia 5.4 (edition of April 2006) and which comprises less than 0.5 μg/g of tin per g of methylene blue. Such a product constitutes another subject of the invention.

The process of the invention is also the only one to give access to a methylene blue or tetramethylthionine chloride which has a degree of purity of greater than 97%, preferably greater than 98%, even better greater than 99%, measured by HPLC under the conditions of the European Pharmacopeia 5.4 (edition of April 2006) and which comprises less than 0.95 μg/g of chromium, advantageously less than 0.90 μg/g, even better less than 0.80 μg/g per g of methylene blue.

The process of the invention is the only one to give access, in an industrial amount, to a methylene blue or a tetramethylthionine chloride comprising less than 3% of impurities, preferably less than 2%, even better less than 1%, measured by HPLC under the conditions of the European Pharmacopeia 5.4 (edition of April 2006) and a level of metal impurities of less than 20 μg/g, advantageously less than 15 μg/g, even more advantageously less than 10 μg/g.

Another subject of the invention is a compound of formula (I), with the exclusion of methylene blue or tetramethylthionine chloride and comprising an overall level of metal impurities of less than 100 μg/g, advantageously less than 50 μg/g, in particular less than 30 μg/g. Preferably, this compound meets one or more of the following requirements:

purity greater than 97%, preferably greater than 98%, even better greater than 99%, measured by HPLC under the conditions of the European Pharmacopeia 5.4 (edition of April 2006), aluminum level of less than 5 μg/g, advantageously less than 4 μg/g, even more advantageously less than 3 μg/g, cadmium level of less than 0.1 μg/g, advantageously less than 0.05 μg/g, even better less than 0.02 μg/g, tin level of less than 0.5 μg/g, advantageously less than 0.4 μg/g and even more advantageously less than 0.3 μg/g.

Methylene blue has been used for decades in the treatment of various infections. It is used as an antiseptic, anti-infective, as an antidote and as a diagnostic agent. Recently, its antiviral activity has been demonstrated, and it could be used in the preparation of a medicament for combating a pathological condition such as an infection, in particular a septic shock, the presence of pathogenic contaminants in the blood or the plasma, an exaggerated hemodynamic reaction, an infection with HIV, West Nile virus or the hepatitis C virus, Alzheimer's disease, malaria, breast cancer or manic depressive disorders.

Finally, it could also be used in cosmetics or for products for ophthalmic application.

For all these therapeutic uses, and in particular in the context of the prevention and treatment of Alzheimer's disease, it is necessary to have a methylene blue which has a high degree of purity and in particular which comprises very few metal impurities.

A medicament comprising a methylene blue of the invention, in a pharmaceutically acceptable carrier, constitutes another subject of the invention.

The carrier and the amounts of methylene blue to be administered are well known to those skilled in the art.

Another subject of the invention is a process for preparing a medicament comprising a compound of formula (I), characterized in that this process comprises at least one process step as described above, in particular a step for purification of the compound of formula (I) and/or a step for deprotection of the compound (II) so as to give (I).

Experimental Section

A commercially available methylene blue is purified in accordance with the process of FIG. 1.

1—Synthesis of Benzoyl Leuco Methylene Blue (Step A)

The following are introduced into a 120 l jacketed reactor equipped with a stirrer, and under nitrogen:

80 l of distilled water, 4.2 kg (10.7 mol) of methylene blue sold by the company Leancare Ltd under the reference CI 52015, comprising large amounts of metal impurities (Al, Fe, Cu, Cr).

The mixture is left to stir for 15 min and then 6.9 kg of sodium hydrosulfite $Na_2S_2O_4$ in an aqueous solution at 85% are added. The color changes from blue to beige. The mixture is left to stir for a further 45 min, and then 2.69 kg of sodium hydroxide in the form of pellets are added. The reaction temperature is maintained between 18 and 20° C. The duration of the addition is 30 min and the resulting mixture is left to stir for a further 30 min. 7.90 l of benzoyl chloride are subsequently added dropwise. The reaction mixture turns a green-beige color. The duration of the addition is 2 h and the resulting mixture is then left to stir for 20 h.

Treatment:

After the stirring has been stopped, the mixture is allowed to separate by settling out for 15 min and the supernatant is drawn up. 80 l of water (25 volumes) are added and, after stirring and separation by settling out, the supernatant is again drawn up. 24 l of EtOH are added and, after stirring for approximately 5 min, 16 l of water are added. After having stirred for 15 min, the mixture is filtered through a receiver. This operation is repeated 3 times. After drying, 2.9 kg (yield: 66%) of benzoyl leuco methylene blue are obtained.

2—Purification 4.25 kg of benzoyl leuco methylene blue derived from the first step, solubilized in 30 l of $CH_2Cl_2$, are used. The solution is filtered through 3 parts of silica (Merck Gerudan Si60) (11.5 kg) and 0.5 kg of Fontainebleau sand, with rinsing being carried out with 30 liters of $CH_2Cl_2$. The $CH_2Cl_2$ is removed by evaporation under vacuum. 6 l of ethanol are added. The mixture is left to stir in the cold and then filtered through a receiver. The resulting product is dried under vacuum. 3.4 kg of purified benzoyl leuco methylene blue are obtained (yield: 80%).

Purity: +99% HPLC

Metals: the content of metals (in µg/g) is given for 3 tests in table 1.

TABLE 1

| Test | Test 1 | Test 2 | Test 3 |
|---|---|---|---|
| Al | 0.5 | 0.5 | 0.1 |
| Cu | 0 | 0 | 0.4 |
| Fe | 0 | 0 | 0.1 |
| Zn | 0.9 | 0.7 | 0.5 |
| Ni | 0.1 | 0.1 | 0.1 |
| Cr | 0.3 | 0.3 | 0.03 |
| Mo | 0.1 | 0.1 | 0.1 |
| Mn | 0.02 | 0 | 0 |
| Sn | 0.5 | 0.4 | 0.5 |
| Pb | 5 | 3.2 | 2.4 |
| Cd | 0.2 | 0.2 | 0.07 |

3—Debenzoylation

The following are introduced into a 100 l jacketed enameled reactor at ambient temperature:

45 l of acetonitrile (ACN), 1.6 kg of benzoyl leuco methylene blue derived from the second step, and stirred. The mixture is allowed to stir for 30 min at ambient temperature and then the temperature is decreased to −18° C. 950 g of DDQ solubilized in 4 l of ACN are added in one portion. The mixture is left to stir for 2 h at −18° C. Filtration is performed. A complex of the 3,7-bis(dimethylamino)phenothiazine with the DDQ is obtained and is used directly in the subsequent step.

4—Salification

The cake derived from the third step is reintroduced, in several pieces, into the jacketed enameled reactor. 4 l of EtOAc are added. The mixture is left to stir for 30 min at ambient temperature. The temperature is decreased to −18° C. 2.5 kg of HCl in 16 l of EtOAc (4N solution) are added. The mixture is stirred for 2 h at −18° C. The mixture is filtered and then the cake is reintroduced into the reactor. 30 l of EtOAc are added at −18° C. and the mixture is again filtered.

5—Neutralization 30 l of acetone are added, followed by a solution of 200 g of NaOH solubilized in 500 ml of water. The mixture is filtered. The product derived from the fourth step is introduced into the reactor with 30 l of acetone. The medium is stirred for 1 h at ambient temperature. The pH is 4.0. The medium is filtered. It is left under vacuum on the receiver.

6—Purification and Hydration 1.9 kg of the product from the fifth step and 30 l of a 50/50 mixture of $CH_2Cl_2$/EtOH are introduced into a 40 l enameled reactor under $N_2$, at ambient temperature. The resulting mixture is refluxed (43° C.). It is filtered under hot conditions with a microfiber filter (Whatman GF/D). This operation is carried out twice. The reactor is cleaned with demineralized water. The filtrate is reintroduced into the reactor. 24 liters of solvent are distilled under vacuum at 28° C. (3 h). The medium is put back into the reactor. 1 l of microfiltered water is added. The mixture is cooled to −18° C. 40 l of EtOAc are added and the resulting mixture is left stirring overnight in the cold. It is filtered. It is made into a paste with 10 l of EtOAc. 1.4 kg of purified methylene blue in the trihydrate form are obtained.

The metal impurities are analyzed and reported in table 2.

TABLE 2

| Element | Amount (µg/g) |
|---|---|
| Al | 1.3 |
| Cu | 0.5 |
| Fe | 1.9 |
| Zn | 1.7 |
| Ni | 0.5 |
| Cr | 0.8 |
| Mo | 0.2 |
| Mn | 0.08 |
| Sn | 0.4 |
| Pb | 0.1 |
| Cd | 0.04 |

The invention claimed is:

1. A methylene blue (3,7-bis(dimethylamino)phenothiazin-5-ylium chloride) comprising less than 3% of impurities measured by HPLC under the conditions of the European Pharmacopeia 5.4 and less than 20 µg/g of total metal content.

2. A methylene blue according to claim 1 wherein it comprises less than 15 µg/g of total metal content.

3. A methylene blue according to claim 1 wherein it comprises less than 10 µg/g of total metal content.

4. A methylene blue according to claim 1, wherein it comprises 0.02 µg or less of cadmium per g of methylene blue.

5. A methylene blue according to claim 1, wherein it comprises less than 4.5 µg/g of aluminum.

6. A methylene blue according to claim 1, wherein it comprises less than 2.5 µg/g of aluminum.

7. A methylene blue according to claim 1, wherein it comprises less than 0.5 g/g of tin.

8. A methylene blue according to claim 1, wherein it comprises less than 0.3 µg/g of tin.

9. A methylene blue according to claim 1, wherein it comprises 0.95 µg or less of chromium per g of methylene blue.

10. A methylene blue according to claim 1, wherein it is obtained by a method which comprises at least one step during which a compound of formula (II):

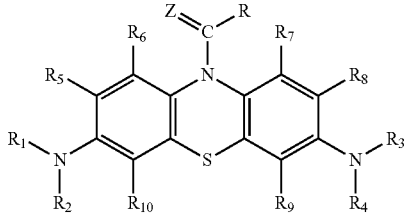

in which
each of $R_1$, $R_2$, $R_3$, $R_4$ represent a methyl group,
each of $R_5$, $R_6$, $R_7$, $R_8$, $R_9$ and $R_{10}$ represent a hydrogen atom,
R represents a group chosen from:
  a phenyl or benzyl group, optionally substituted with one or more functions chosen from: a $C_1$-$C_4$ alkyl, a halogen atom, a $C_1$-$C_4$ haloalkyl and a nitro group,
  a phenyloxy or benzyloxy group optionally substituted on the aromatic nucleus with one or more functions chosen from: a $C_1$-$C_4$ alkyl, a halogen atom, a $C_1$-$C_4$ haloalkyl and a nitro group,
  Z represents an atom chosen from O and S,
  is subjected to a purification step under conditions which make it possible to separate metal compounds from the compounds of formula (II), wherein the purification step comprises at least one filtration through a support capable of retaining the metal compounds, and the filtration support is chosen from: a silica gel, a neutral, basic or acidic alumina gel, a microporous membrane, a resin grafted with metal-capturing groups, and fibers grafted with metal-capturing groups,
  and said method further comprises at least one step during which the compound of formula (II) is subjected to a step for deprotection of the R—CZ group from the amine of the phenothiazine ring.

11. A methylene blue according to claim 10, wherein in formula II Z represents O and R represents a phenyl.

12. A methylene blue according to claim 1, wherein it is obtained by a method which comprises at least one step during which a compound of formula (II):

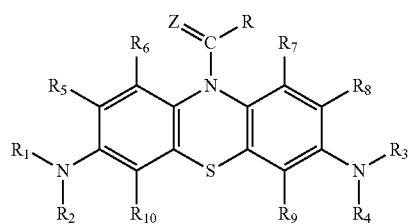

in which
each of $R_1$, $R_2$, $R_3$, $R_4$ represent a methyl group,
each of $R_5$, $R_6$, $R_7$, $R_8$, $R_9$ and $R_{10}$ represent a hydrogen atom,
R represents a group chosen from:
  a phenyl or benzyl group, optionally substituted with one or more functions chosen from: a $C_1$-$C_4$ alkyl, a halogen atom, a $C_1$-$C_4$ haloalkyl and a nitro group,
  a phenyloxy or benzyloxy group optionally substituted on the aromatic nucleus with one or more functions chosen from: a $C_1$-$C_4$ alkyl, a halogen atom, a $C_1$-$C_4$ haloalkyl and a nitro group,
  Z represents an atom chosen from O and S,
  is subjected to a purification step under conditions which make it possible to separate metal compounds from the compounds of formula (II), wherein the purification step comprises at least one filtration through a support capable of retaining the metal compounds, and the filtration support is chosen from: a silica gel, a neutral, basic or acidic alumina gel, a microporous membrane, a resin grafted with metal-capturing groups, and fibers grafted with metal-capturing groups, and wherein said method further comprises at least one step wherein the compound of formula (II) is subjected to a step for deprotection of the R—CZ group from the amine of the phenothiazine ring using deprotection means chosen from: quinones.

13. A methylene blue according to claim 12, wherein the deprotection means is 2,3-dichloro-5,6-dicyano-1,4-benzoquinone (DDQ).

14. A medicament comprising a methylene blue as claimed in claim 1, in a pharmaceutically acceptable carrier.

* * * * *

UNITED STATES PATENT AND TRADEMARK OFFICE
CERTIFICATE OF CORRECTION

| | |
|---|---|
| PATENT NO. | : 8,815,850 B2 |
| APPLICATION NO. | : 13/552738 |
| DATED | : August 26, 2014 |
| INVENTOR(S) | : Feraud et al. |

It is certified that error appears in the above-identified patent and that said Letters Patent is hereby corrected as shown below:

In The Claims

Column 10,
Line 63, "less than 0.5 g/g of tin." should read --less than 0.5 µg/g of tin.--.

Signed and Sealed this
Twentieth Day of January, 2015

Michelle K. Lee
*Deputy Director of the United States Patent and Trademark Office*